(12) United States Patent
Forrest

(10) Patent No.: US 8,968,001 B2
(45) Date of Patent: Mar. 3, 2015

(54) FORREST SPONGE AIDED SINUS MEMBRANE LIFT TECHNIQUE

(75) Inventor: Arthur Thomas Forrest, Chino, CA (US)

(73) Assignee: Arthur Thomas Forrest, Chino, CA (US)

( * ) Notice: Subject to any disclaimer, the term of this patent is extended or adjusted under 35 U.S.C. 154(b) by 0 days.

(21) Appl. No.: 13/421,794

(22) Filed: Mar. 15, 2012

(65) Prior Publication Data
US 2012/0244499 A1    Sep. 27, 2012

Related U.S. Application Data

(60) Provisional application No. 61/466,431, filed on Mar. 22, 2011.

(51) Int. Cl.
| | | |
|---|---|---|
| *A61C 8/00* | (2006.01) | |
| *B25B 13/48* | (2006.01) | |
| *A61L 27/18* | (2006.01) | |
| *A61L 27/56* | (2006.01) | |
| *B25B 21/00* | (2006.01) | |
| *B25B 23/14* | (2006.01) | |

(52) U.S. Cl.
CPC ............... *B25B 13/48* (2013.01); *A61C 8/0092* (2013.01); *A61L 27/18* (2013.01); *A61L 27/56* (2013.01); *B25B 21/008* (2013.01); *B25B 23/14* (2013.01)

USPC ........................................................ 433/173

(58) Field of Classification Search
USPC .................................................. 433/172–176
See application file for complete search history.

(56) References Cited

U.S. PATENT DOCUMENTS

2012/0159729 A1 *   6/2012   Armaly, Jr. ..................... 15/118

* cited by examiner

*Primary Examiner* — Sunil K Singh

(57) ABSTRACT

The invention involves the use of pre-calculated and pre-formed, specific forms of medical grade polyurethane foam for sinus membrane surgery by a dentist, physician, or veterinarian, as a non-cutting surgical instrument. The invention uses various shapes to do the job of safely and gently releasing free, predetermined membrane thicknesses of sinus membranes from the boney sinus floor and sinus walls. Sinus surgery is made safer and simpler, even those with a challenging anatomy. The scope of the invention is, therefore, indicated by the claims rather than the foregoing description. Furthermore, the present invention may utilize other specific sponge forms without departing from the spirit of essential characteristics. The forms and shapes and the various sized components are merely exemplary and can be varied to preferred surgical osteotomy and still fall within the scope of the invention. The scope of the invention will be determined only by the claims.

1 Claim, 4 Drawing Sheets

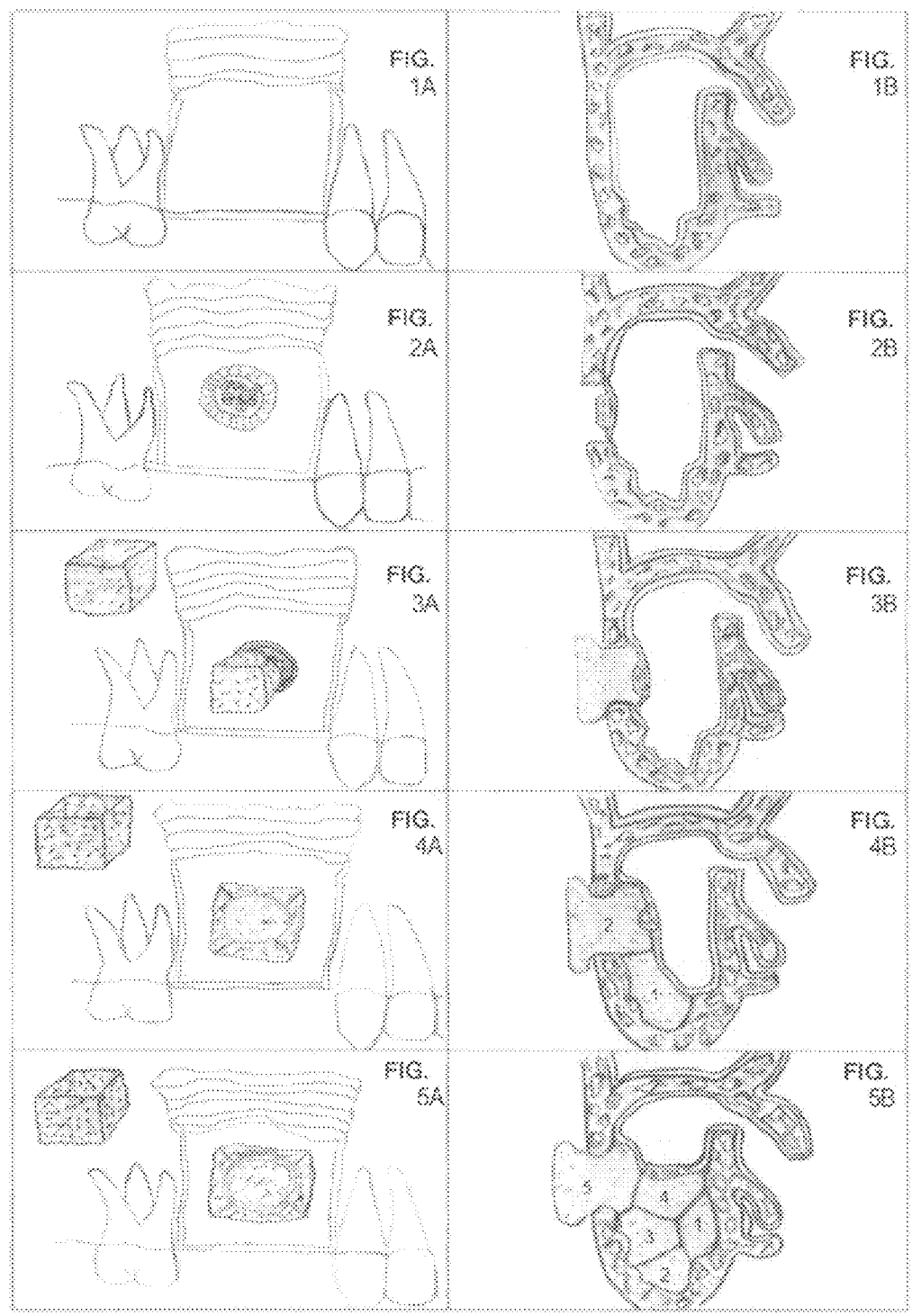

FORREST SPONGE AIDED SINUS MEMBRANE LIFT TECHNIQUE

CROSS-REFERENCE OR RELATED APPLICATIONS

This application claims benefit of Provisional Application 61/466,431 filed on Mar. 22, 2011.

STATEMENT REGARDING FEDERALLY SPONSORED RESEARCH OR DEVELOPMENT (IF APPLICABLE)

Not applicable

REFERENCE TO SEQUENCE LISTING, A TABLE, OR A COMPUTER PROGRAM LISTING COMPACT DISK APPENDIX, (IF APPLICABLE)

Not applicable

BACKGROUND OF THE INVENTION

In the professional and surgical field of implant dentistry there are many surgical and anatomical barriers. In the maxillary arch when teeth are missing. Often there is deficient bone quantity to totally cover or stabilize dental implants. The dental implants cannot be placed unless more advanced regenerative bone grafting surgeries are initiated. In all of the surgeries the sinus membrane must be lifted in order to place the bone grafting material. My invention of the sponge aided lifting technique is a simpler and less traumatic technique, of performing the surgery. Unlike the classical technique, it does not involve a complicated and sophisticated use of many multi-curved curette knives; with the ever looming fear of cutting, or penetration of the membrane. It also is not a blind technique utilizing balloons or water pressure in an unknown and unseen environment with possible unknown tears to the membrane. It is a simpler, easier and more control technique, both for the novice and for the experienced surgeon. Because the sponges are so soft, they slowly lift the membrane without trauma. The need for a larger surgical opening to the sinus is eliminated because a much smaller opening is all that is necessary to use a sponge technique. The patient suffers less trauma and morbidity. The sponge technique can be used with any amount of remaining bone from the smallest 1 mm or less, to the larger six or 7 mm thick boney floors. There are no limitations as there is with other specialized sinus techniques used. Once learned about the degree of ease and safety, the sponge aided technique will replace how sinus surgery is a preform around the world. The safety and simplicity of the sponge aided technique will become an intrinsic safety tool for every worldwide surgeon's surgical sinus technique.

Synthetic sponge cubes, or truncated rectangles, cylinders or cones sponge shapes, made of medical grade dense polyurethane foam material that are used to gently and safely lift up the surgically exposed Schneiderian membrane off of the sinus floor and walls without the use of sharpen sinus curette knifes. Sponges allow and give total operator controlled gentle membrane lifting force motion. The membrane is lifted softly and atraumatically with visualization. These soft polyurethane foam sponges will continue to rebound and expand when they are first placed in compressed state. When you softly wiggle more than one into the contained space of the sinus they will continue to softly enlarge the space in mass by lifting the membrane off of the bony floor and wall without surgical trauma. The soft sponge will safely negotiate bony projections and any other types of obstacles. This is because the sponges easily conform to the shape of the sinus bony contours while it lifts the membrane off the sinus floor and walls. Another surgical bonus is because this sponges do the work the surgeon does not have to create a larger surgical opening in this sinus to physically manipulate the typical specialized large array of surgical sinus knives. Just like the wire twisted compression springs that are used in orthodontics, the size of the cubes and cones act as soft sponge "springs" to help gently lift the sinus membrane off of the sinus bony with floor and walls. When compressed to one half their normal size, each sponge will create a force of expansion or rebound of 40 up to 65 g. This force will softly with decreasing force as they fully expand lift the membrane off of the sinus bone. Everything is under the surgeon's complete visual and tactile control unlike other blind crestal approach techniques.

BRIEF SUMMARY OF THE INVENTION

My invention, Forrest Sponge Aided Sinus Lift Technique involves the use of special synthetic sponges of various small cubes, rectangles and truncated rectangular sizes, made of medical grade dense polyurethane foam material, which is used to lift the membrane off of the sinus bony floor and walls. This is done without the normal scrapping—cutting surgery of the membrane—bone interface (therefore less morbidity and less trauma and faster healing). The soft expansion work of the sponges make the very technique sensitive procedure of using curette knives to lift the membrane obsolete, and not needed! It is the use of the curette knives that causes 80% of most of the membrane perforation damage during the sinus lift surgery. The purpose of this sponge is to make easy one of the most difficult, complicated and delicate surgeries in all of implant dentistry, the sinus membrane lift surgical procedure, simple with predictable safe results every time.

BRIEF DESCRIPTION OF THE SEVERAL VIEWS OF THE DRAWINGS

Description of Numbered Drawings: Page 1/4

FIG. 1A. Shows the lateral external view of the sinus wall at surgery

FIG. 1B. The sliced frontal plane section of sinus showing typical complication areas.

FIG. 2A. Sinus surgery with ring of membrane exposed with bone segment still attached.

FIG. 2B. Frontal view of before entry start into sinus interior.

FIG. 3A. Showing a typical sponge sinus cube at the time of first soft "wiggled" entry.

FIG. 3B. Illustrating the sinus membrane being gently lifted.

FIG. 4A Shows second sinus sponge cube at placement on top of sponge number one.

FIG. 4B. Frontal plane of two sponge cubes being placed inside of sinus.

FIG. 5A. Example of up to a fifth sponge cube being placed.

FIG. 5B. Typical view of multiple sponges (5) completely and softly lifting of the sinus membrane without tears or perforations, without the use of knives.

Figure 6A:
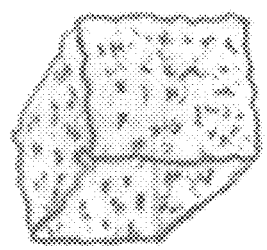
FIG. 6A. Large 15 mm×15 mm square sponge
Figure 6B:
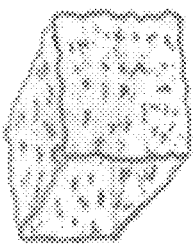
FIG. 6B. Medium 10 mm×15 mm rectangle sponge
Figure 6C:
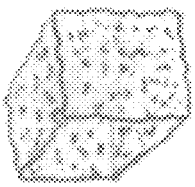
FIG. 6C. Small 10 mm×10 mm cube sponge
Figure 7:
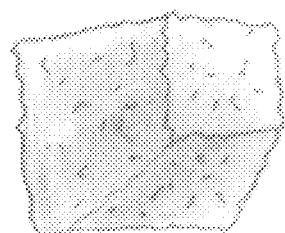
FIG. 7. Large 15 mm×15 mm truncated sponge.
Figure 8A:
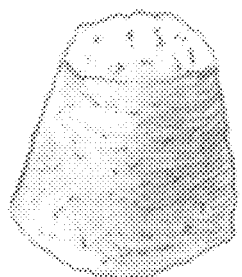
FIG. 8A. Medium 15 mm×10 mm cone sponge.
Figure 8B:
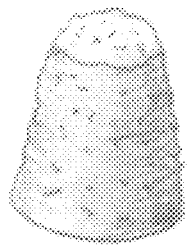
FIG. 8B. Small 10 mm by 8 mm cone sponge
FIG. 9A. Large 15 mm×15 mm cylinder sponge.
Figure 9A:
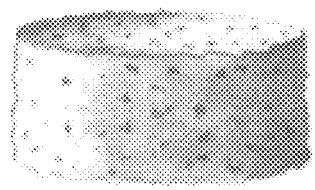
FIG. 9B. Medium 15 mm×10 mm cylinder sponge.
FIG. 9C. Small 10 mm by 8 mm cylinder sponge Detailed Description of the Invention The Forrest Sponge Aided Sinus Membrane Lift Technique is an unique invention that can totally change the methods of sinus surgery around the world. Through the unique use of specialized shaped medical grade sterile polyurethane foam, the most difficult and technical surgery in all of dentistry is made safe and predictable. The uses of specialty shaped knives are eliminated. The use of the knives has been estimated to cause 80% of the sinus membranes perforations. The sponges can eliminate 80% of the greatest cause of sinus surgery failures. No other currently known sinus surgery technique can work as predictable as the sponge aided sinus membrane lift technique. The sponges with their unique configurations can be used with most all sinus surgery techniques. The small cubes and the small cones can easily be used as starter sponges without causing undue force during their placement. Remember unlike other techniques the surgeons-operator has full visual and tactile control of sponge placement See FIGS. 3A and 4B. On a very thin sinus membrane, an extremely soft wiggling motion should be used to place the sponge without fear of perforation. The same amount of easy slow force is used to place subsequent sponges. The force of action of the sponge is related to the size of the sponge used. Each square or rectangular or cylindrical sponge shape is made from a die cut stamp, from a roll or sheet of specific uniform thickness medical grade polyurethane foam. Truncated polygons and Cones shapes may require die molds. These specialty shapes are for the irregular sinus spaces, although any shaped sponge will mold and conform itself to any shaped sinus cavity, see FIGS. 6A-9C.
Figure 9B:
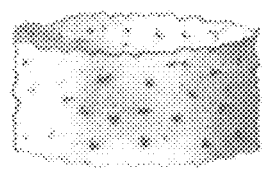
Figure 9C:
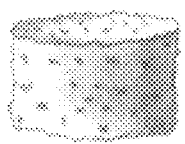

Because the sponges will do the actual lifting work a smaller sized sinus access opening can be utilized. The smaller size means less morbidity. A good working technique is to use the smaller size sponges first to create the initial safe lifting sized area, remove them after two or three are placed, then, replace them with larger size sponges to complete the task. The larger size sponges will be more readily in reach and more easily seen and removed when time to remove them is necessary. If the sponges are left in place for more than 5 min. the membrane loses quite a bit of its elasticity and just flops gently. There would be no need in worrying about small sponges being lost with the larger replacement technique. But if one wanted to, one could use a sterile 3-0 suture to suture to each sponge cubes like beads on necklace before placement to ensure removal. Remember the protocol is to count each sponge at removal. Although the sponges are sterile, one could wet them with an antibiotic solution at time of placement to help treat for and prevent possible opportunistic infections or even the wetting with anesthetic for hemostasis control.

The invention claimed is:

1. A method of lifting the sinus membrane from a sinus bone without the use of sinus curette knives, the method comprises:
    inserting at least one polyurethane foam sponge into the sinus cavity;
    moving the at least one polyurethane foam sponge within the space of the sinus cavity causing the sponge to expand and lift the sinus membrane off of the sinus bone without surgical trauma caused by curette knives.

* * * * *